US012741000B2

(12) United States Patent
He et al.

(10) Patent No.: US 12,741,000 B2
(45) Date of Patent: Sep. 22, 2026

(54) TRADITIONAL CHINESE MEDICINE COMPOSITION FOR TREATING PSORIASIS, PREPARATION METHOD THEREFOR AND USE THEREOF

(71) Applicant: TASLY PHARMACEUTICAL GROUP CO., LTD., Tianjin (CN)

(72) Inventors: Yi He, Tianjin (CN); Shuiping Zhou, Tianjin (CN); Yu Wang, Tianjin (CN); Yuanpeng Jin, Tianjin (CN); Jinghua Kang, Tianjin (CN); Zhipeng Huo, Tianjin (CN); Zhijuan Huang, Tianjin (CN); Yuanxue Liu, Tianjin (CN); Zhaohui Song, Tianjin (CN)

(73) Assignee: TASLY PHARMACEUTICAL GROUP CO., LTD., Tianjin (CN)

( * ) Notice: Subject to any disclaimer, the term of this patent is extended or adjusted under 35 U.S.C. 154(b) by 847 days.

(21) Appl. No.: 17/776,603

(22) PCT Filed: Nov. 10, 2020

(86) PCT No.: PCT/CN2020/127872
§ 371 (c)(1),
(2) Date: May 13, 2022

(87) PCT Pub. No.: WO2021/098557
PCT Pub. Date: May 27, 2021

(65) Prior Publication Data

US 2022/0395539 A1 Dec. 15, 2022

(30) Foreign Application Priority Data

Nov. 19, 2019 (CN) ......................... 201911138396.5

(51) Int. Cl.

| | |
|---|---|
| ***A61K 36/539*** | (2006.01) |
| ***A61K 9/00*** | (2006.01) |
| ***A61K 33/06*** | (2006.01) |
| ***A61K 35/36*** | (2015.01) |
| ***A61K 36/355*** | (2006.01) |
| ***A61K 36/484*** | (2006.01) |
| ***A61K 36/65*** | (2006.01) |
| ***A61K 36/739*** | (2006.01) |
| ***A61K 36/744*** | (2006.01) |
| ***A61P 17/06*** | (2006.01) |

(52) U.S. Cl.
CPC ............ *A61K 35/36* (2013.01); *A61K 9/0053* (2013.01); *A61K 33/06* (2013.01); *A61K 36/355* (2013.01); *A61K 36/484* (2013.01); *A61K 36/539* (2013.01); *A61K 36/65* (2013.01); *A61K 36/739* (2013.01); *A61K 36/744* (2013.01); *A61P 17/06* (2018.01); *A61K 2236/331* (2013.01)

(58) Field of Classification Search
None
See application file for complete search history.

(56) References Cited

FOREIGN PATENT DOCUMENTS

| | | | | |
|---|---|---|---|---|
| CN | 1954847 | A | | 5/2007 |
| CN | 101057896 | A | | 10/2007 |
| CN | 101190320 | A | | 6/2008 |
| CN | 101322775 | A | | 12/2008 |
| CN | 101327231 | A | | 12/2008 |
| CN | 101601783 | A | | 12/2009 |
| CN | 101623343 | A | | 1/2010 |
| CN | 101658616 | A | | 3/2010 |
| CN | 101700391 | A | | 5/2010 |
| CN | 1954847 | B | * | 9/2010 |
| CN | 101874867 | A | | 11/2010 |
| CN | 102240336 | A | | 11/2011 |
| CN | 102266435 | A | | 12/2011 |
| CN | 102309627 | A | | 1/2012 |
| CN | 102319293 | A | | 1/2012 |
| CN | 102362951 | A | | 2/2012 |
| CN | 102579895 | A | | 7/2012 |
| CN | 102579917 | A | | 7/2012 |
| CN | 102688420 | A | | 9/2012 |
| CN | 102727801 | A | | 10/2012 |
| CN | 102885968 | A | | 1/2013 |

(Continued)

OTHER PUBLICATIONS

China Patent Application No. 201911138396.5; Office Action; dated Nov. 28, 2022; 10 pages.

(Continued)

*Primary Examiner* — Anand U Desai
*Assistant Examiner* — Catheryne Chen
(74) *Attorney, Agent, or Firm* — BakerHostetler

(57) ABSTRACT

A traditional Chinese medicine composition for treating psoriasis, a preparation method therefor and a use thereof. The traditional Chinese medicine composition comprises: water buffalo horn powder, Japanese honeysuckle flower, gypsum, red peony root, peony bark, charred cape jasmine fruit, baical skullcap root, raw garden burnet root, and liquorice root. The preparation method comprises: proportionally weighing out the baical skullcap root, the Japanese honeysuckle flower, the red peony root, the peony bark, the gypsum, the charred cape jasmine fruit, the garden burnet root and the liquorice root, adding water and decocting 1 to 3 times, each time using 4 to 10 times the amount (weight to volume ratio) of water and decocting for 0.5 to 3 hours; combining decoctions, filtering, vacuum concentrating the filtrate, drying same, adding the water buffalo horn powder and mixing until evenly distributed.

9 Claims, No Drawings

(56) References Cited

FOREIGN PATENT DOCUMENTS

| | | | |
|---|---|---|---|
| CN | 102949511 | A | 3/2013 |
| CN | 103349701 | A | 10/2013 |
| CN | 103505667 | A | 1/2014 |
| CN | 103784641 | A | 5/2014 |
| CN | 103800589 | A | 5/2014 |
| CN | 103860743 | A | 6/2014 |
| CN | 103893632 | A | 7/2014 |
| CN | 104027672 | A | 9/2014 |
| CN | 104306833 | A | 1/2015 |
| CN | 104383435 | A | 3/2015 |
| CN | 104524148 | A | 4/2015 |
| CN | 104587267 | A | 5/2015 |
| CN | 104606599 | A | 5/2015 |
| CN | 104645143 | A | 5/2015 |
| CN | 104666588 | A | 6/2015 |
| CN | 104689132 | A | 6/2015 |
| CN | 104689254 | A | 6/2015 |
| CN | 104707029 | A | 6/2015 |
| CN | 104721405 | A | 6/2015 |
| CN | 104758444 | A | 7/2015 |
| CN | 104771666 | A | 7/2015 |
| CN | 104971312 | A | 10/2015 |
| CN | 105031012 | A | 11/2015 |
| CN | 105056016 | A | 11/2015 |
| CN | 105125712 | A | 12/2015 |
| CN | 105148186 | A | 12/2015 |
| CN | 105213971 | A | 1/2016 |
| CN | 105596767 | A | 5/2016 |
| CN | 105687343 | A | 6/2016 |
| CN | 105833059 | A | 8/2016 |
| CN | 105833135 | A | 8/2016 |
| CN | 105902852 | A | 8/2016 |
| CN | 105902908 | A | 8/2016 |
| CN | 105920246 | A | 9/2016 |
| CN | 105943738 | A | 9/2016 |
| CN | 105943946 | A | 9/2016 |
| CN | 105944001 | A | 9/2016 |
| CN | 105963374 | A | 9/2016 |
| CN | 106138495 | A | 11/2016 |
| CN | 106177583 | A | 12/2016 |
| CN | 106177832 | A | 12/2016 |
| CN | 106266740 | A | 1/2017 |
| CN | 106344768 | A | 1/2017 |
| CN | 106491908 | A | 3/2017 |
| CN | 106668269 | A | 5/2017 |
| CN | 106668554 | A | 5/2017 |
| CN | 106728751 | A | 5/2017 |
| CN | 106822367 | A | 6/2017 |
| CN | 106902275 | A | 6/2017 |
| CN | 107115405 | A | 9/2017 |
| CN | 107137639 | A | 9/2017 |
| CN | 107582926 | A | 1/2018 |
| CN | 107802650 | A | 3/2018 |
| CN | 108186863 | A | 6/2018 |
| CN | 108187016 | A | 6/2018 |
| CN | 108434342 | A | 8/2018 |
| CN | 108635536 | A | * 10/2018 |
| CN | 108926641 | A | 12/2018 |
| CN | 109172641 | A | 1/2019 |
| CN | 109260382 | A | 1/2019 |
| CN | 110101765 | A | 8/2019 |
| KR | 1020180104516 | A | 9/2018 |

OTHER PUBLICATIONS

Lei, Dawei; "Analysis of Curative Effect of Qingkailing on 26 Cases of Psoriasis"; Chinese Community Physician; vol. 21 No. 276; 2005; p. 41 (contains English Translation).

Xiaobo Jia et al., Chief Physician Zhiming Zhang's Practical Experiences in Treating Severe Psoriasis, JETCM. Apr. 2015, vol. 24, No. 4, 644-646.

Shangjian Sun, Collection of Clinical Practices from TCM Professor Chaofan Zhou, 136-138, Jan. 31, 2009.

Wei Li et al., Drugs for Improving Blood Circulation Should Be Used with Caution in the Treatment of Psoriasis, Journal of Sichuan of TCM, 2004, vol. 22, No. 7,33-34.

* cited by examiner

TRADITIONAL CHINESE MEDICINE COMPOSITION FOR TREATING PSORIASIS, PREPARATION METHOD THEREFOR AND USE THEREOF

CROSS-REFERENCE TO RELATED APPLICATIONS

The present application is a U.S. National Phase Entry of International PCT Application No. PCT/CN2020/127872 having an international filing date of Nov. 10, 2020, which claims priority to Chinese Patent Application No. 201911138396.5 filed on Nov. 19, 2019. The above-identified applications are hereby incorporated by reference in their entirety.

TECHNICAL FIELD

The present application relates to but is not limited to a traditional Chinese medicine composition, in particular to but not limited to a traditional Chinese medicine composition for treating psoriasis, and a preparation method and use thereof.

BACKGROUND

Psoriasis, commonly known as serpedo, is a common and easily-recurrent inflammatory skin disease whose cause is not fully understood. The typical pathological changes are hyperproliferation and obstruction of differentiation of epidermis. The clinical symptom is that there are multi layers of silvery white scales attached to erythema, which is characterized by the long course of disease, obstinacy and high recurrence rate. At present, it has been found in researches that men and women of all ages can be affected by the disease, and about 80% of them are young and middle-aged patients, and the incidence rate is increasing year by year. This disease is one of the most important diseases that researches are focused on in the field of dermatology at present. The disease seriously affects the quality of life of patients.

At present, there is no especially good cure for psoriasis. Western medicine treatment mainly relieves symptoms, but has relatively significant toxic and side effects, such as vitamin D3 analogues, glucocorticoids, methotrexate, immunosuppressants and so on. Therefore, researchers are seeking for a traditional Chinese medicine composition for treating psoriasis which can completely cure psoriasis and has low toxic and side effects from the perspective of traditional Chinese medicine.

According to the theory of traditional Chinese medicine, psoriasis originates from "exogenous pathogenic wind-cold, moisture and heat-toxin, which are blocked in the skin; exogenous pathogeny enters into the interior and transforms into heat, or overeating spicy, fatty and sweet foods leads to internal heat, internal and external pathogeny accumulates in blood, and blood heat is generated". Excessive heat hurts the blood vessels, excessive heat forces blood to run rashly, yang vessel damage leads to blood overflow, yin vessel damage leads to blood accumulation, off-meridian blood leads to blood stasis, and macules appear on the skin. The more serious the disease is, the darker the macules are, and the lesion site is related to lung and stomach.

Traditional Chinese medicine has the conclusion that "external medicine does not treat tinea and internal medicine does not treat asthma", since asthma and tinea are easy to treat, but they are prone to recurrence and difficult to cure. Many documents, including patents, publicly reported traditional Chinese medicine compositions for treating psoriasis. The following table lists information of some Chinese patents:

| Application number | Application title | Applicant |
|---|---|---|
| 201810266909.X | A traditional Chinese medicine composition for treating psoriasis | Zhang Yanbo |
| 201810183728.0 | A traditional Chinese medicine composition for treating psoriasis | Zhou Jianfu |
| 201710380425.3 | A traditional Chinese medicine composition for treating psoriasis | Lu Wenkui |
| 201810264285.8 | A traditional Chinese medicine for treating psoriasis | Shangqiu Kangdu Dermatology Research Institute |
| 201510566182.3 | A traditional Chinese medicine for treating psoriasis | Huang Jian |
| 201510150239.1 | A traditional Chinese medicine for treating psoriasis | Shandong Provincial Hospital |
| 201410665283.1 | A traditional Chinese medicine composition for treating psoriasis | Han Wenzhi |
| 201610995271.4 | A traditional Chinese medicine composition for treating psoriasis | Chengdu Yuelun Trading Co., Ltd. |
| 201410801154.0 | A traditional Chinese medicine composition for treating psoriasis | Jiang Zili |
| 201510670944.4 | A traditional Chinese medicine composition for treating psoriasis | Guangdong Provincial Hospital of Traditional Chinese Medicine |
| 201610439820.X | A traditional Chinese medicine composition for treating psoriasis | Lin Rongbo |
| 201610439519.9 | A traditional Chinese medicine composition for treating psoriasis | Lin Rongbo |
| 201610100660.6 | A traditional Chinese medicine composition for treating psoriasis | Ding Changyan |
| 201410067802.4 | A traditional Chinese medicine composition for treating psoriasis | Guo Shijiu |
| 201410316680.8 | A traditional Chinese medicine composition for treating psoriasis | Hua Ju |

-continued

| Application number | Application title | Applicant |
|---|---|---|
| 201510524061.2 | A traditional Chinese medicine composition for treating psoriasis | Xu Dan |
| 201710168356.X | A traditional Chinese medicine composition for treating psoriasis | Liu Shining |
| 201510062031.4 | A traditional Chinese medicine composition for treating psoriasis | Gou Xijun |
| 201310127315.8 | A traditional Chinese medicine composition for treating psoriasis | Zhang Aixia |
| 201610398302.8 | A traditional Chinese medicine composition for treating psoriasis | Yin Xiaotong |
| 201710215741.5 | A traditional Chinese medicine composition of external use for treating psoriasis | Zhang Peng |
| 201710518676.3 | A traditional Chinese medicine composition of external use for treating psoriasis | Zhang Ting |
| 201410605958.3 | A traditional Chinese medicine composition of internal use for treating psoriasis | Li Wen |
| 201010186340.X | A traditional Chinese medicine formulation for treating psoriasis | Li Yunxiang |
| 200810138403.7 | A traditional Chinese medicine composition for treating psoriasis | Weifang Oriental Psoriasis Research Institute |
| 201210069977.X | A traditional Chinese medicine for treating psoriasis | Liu Hongpu |
| 201210412496.4 | A traditional Chinese medicine capsule for treating psoriasis | Han Guangxin |
| 201110326428.1 | A traditional Chinese medicine formulation for treating psoriasis | Li Anming |
| 201610322152.2 | A traditional medicine composition for treating psoriasis | Ma Mingdong |
| 201510147494.0 | A traditional Chinese medicine composition for treating psoriasis | Wang Huilan |
| 201510147493.6 | A traditional Chinese medicine composition for treating psoriasis | Wang Huilan |
| 201510118597.4 | A traditional Chinese medicine composition for treating psoriasis | Yu Qing |
| 200910302501.4 | A traditional Chinese medicine composition for treating psoriasis | Deng Mingxiang |
| 201210045249.5 | A traditional Chinese medicine composition for treating psoriasis | Wang Lianfen |
| 201510120257.5 | A traditional Chinese medicine composition for treating psoriasis | Yu Qing |
| 201310635727.2 | A traditional Chinese medicine composition for treating psoriasis | Qingdao Shizhili Institute of Chinese Herbal Medicine |
| 201711097567.5 | A traditional Chinese medicine composition for treating serpedo | Du Haiping |
| 201910324975.2 | A traditional Chinese medicine composition for treating serpedo | Shang Wei |
| 201811327090.X | A traditional Chinese medicine composition for treating serpedo | Jiangxi University of Traditional Chinese Medicine |
| 201710281144.2 | A traditional Chinese medicine composition for treating serpedo | Fan Baoping, Xing Gaimin |
| 201811349672.8 | A traditional Chinese herbal medicine for treating serpedo | Wei Jiancheng |
| 201110185589.3 | A traditional Chinese medicine composition for treating serpedo | Zhang Limin, Zhang Lizhen |
| 201710015077.X | A traditional Chinese medicine composition for treating serpedo | Tang Dingjin |
| 201110205886.X | A traditional Chinese medicine composition for treating serpedo | Pan Jian |
| 201610314600.4 | A traditional Chinese medicine composition for treating serpedo | Quan Yunming |
| 201610439518.4 | A traditional Chinese medicine composition for treating serpedo | Lin Rongbo |
| 201610439533.9 | A traditional Chinese medicine composition for treating serpedo | Lin Rongbo |
| 201710870068.9 | A traditional Chinese medicine composition for treating serpedo | Huang Jingwei |
| 201410151703.4 | A traditional Chinese medicine composition for treating serpedo | Wu Haiming |
| 201510199984.5 | A traditional Chinese medicine composition for treating serpedo | Zhang Changlian |
| 201610354827.1 | A traditional Chinese medicine composition for treating serpedo | Zhang Xiaoyan |

-continued

| Application number | Application title | Applicant |
|---|---|---|
| 201610254366.0 | A traditional Chinese medicine composition for treating serpedo | Zou Hongsheng |
| 201610155261.X | A traditional Chinese medicine composition for treating serpedo | Zhang Yan |
| 201510419653.8 | A traditional Chinese medicine composition for treating serpedo | Shandong Fangjian Pharmaceutical Co., Ltd. |
| 201710170588.9 | A traditional Chinese medicine composition for treating serpedo | Yu Li |
| 201610548477.2 | A traditional Chinese medicine composition for treating serpedo | Zhang Jiqiang |
| 201510169724.3 | A traditional Chinese medicine combination for treating serpedo | Xu Weishan |
| 200910183631.0 | A traditional Chinese medicine for treating serpedo | Sun Bin |
| 201610995409.0 | A traditional Chinese medicine formula for treating serpedo | Chengdu Yuelun Trading Co., Ltd. |
| 201610764938.X | A traditional Chinese medicine of external use for treating serpedo | Huang Rongbo |
| 201410045987.9 | A traditional Chinese medicine for treating serpedo | Zhang Xiaochang |
| 201611214002.6 | A preparation method for a traditional Chinese medicine for treating serpedo | Wang Guixian |
| 200810017116.0 | A traditional Chinese medicine composition for treating serpedo | Wang Yongjun |
| 201010221836.6 | A traditional Chinese medicine composition for treating serpedo | Feng Jianping |
| 201410727102.3 | A traditional Chinese medicine composition of internal use for treating serpedo | Ma Yanchun |
| 200910065396.7 | A traditional Chinese medicine composition for treating serpedo | Zhou Dahong |
| 201310250229.6 | A traditional Chinese medicine composition for treating serpedo | Li Guang |
| 201310360819.4 | A traditional Chinese medicine composition of internal use for treating serpedo | Ma Yanchun |
| 200910230123.3 | A traditional Chinese medicine composition of internal use for treating serpedo | Zhang Chen |
| 201510602115.2 | A traditional Chinese medicine composition of external use for treating serpedo | Xia Tianlin |
| 201510380473.3 | A medicament of external use specially for treating serpedo | Li Qingqiang |
| 201110182299.3 | A traditional Chinese medicine specially for treating serpedo | Zhang Qinglin |
| 201210218617.1 | A traditional Chinese medicine of internal use for treating serpedo | Li Bingguan |
| 200710003569.3 | A traditional Chinese medicine liniment for treating serpedo | Zheng Xiuqin |
| 201510111221.0 | A Chinese medicine of internal use for treating various intractable serpedo | Lan Jianguo |
| 201210085302.4 | A traditional Chinese medicine decoction for treating serpedo | Lu Aiping |
| 200710014717.1 | A traditional Chinese medicine infusion granule for treating serpedo | Li Mingjun |
| 201110299759.0 | A traditional Chinese medicine preparation for treating serpedo | Li Yuxuan |
| 200510015622.2 | A medicament for treating serpedo | Kang Jinghua |

Among them, Chinese patent 200510015622.2, publication number: CN1954847A discloses a medicine for treating serpedo, which consists of 15-45 parts of buffalo horn powder, 25-30 parts of gypsum (*Gypsum fibrosum*; sheng shi gao), 10-15 parts of rehmannia root (*Rehmanniae radix*; sheng di), 10-15 parts of red peony root (*Paeoniae radix rubra*; chi shao), 10-15 parts of tree peony bark (*Moutan cortex*; dan pi), 25-45 parts of lalang grass rhizome (*Imperatae rhizoma*; bai mao gen), 15-30 parts of Japanese honeysuckle flower (*Lonicerae japonicae flos*; jin yin hua), 10-15 parts of baical skullcap root (*Scutellariae radix*; huang qin), 10-20 parts of Chinese cork-tree (*Phellodendri chinensis Cortex*; huang bo), 10-15 parts of charred cape jasmine fruit (*Gardenias fructus* Praeparatus; jiao zhi zi), 10-15 parts of Danshen root (*Salviae miltiorrhizae radix* et *rhizoma*; dan shen), 15-25 parts of Paris rhizome (*Paridis rhizoma*; zao xiu) and 6-10 parts of liquorice root (*Glycyrrhizae radix* et *rhizoma*; gan cao). In this prescription, buffalo horn powder is used instead of rhinoceros horn to remove heat toxin from the nutrient aspect and the blood aspect, to cool the blood and to eliminate macules; baical skullcap root is used to purge lung fire, Chinese cork-tree is used to purge the fire of the lower energizer, charred cape jasmine fruit is used to purge the fire of the triple energizer, and the combination of the four ingredients plays a role as the sovereign. Gypsum is used to purge lung fire, stomach fire, penetrate muscle heat to eliminate macules; Japanese honeysuckle flower is used to clear heat and toxin, penetrate heat to the outside, lalang grass rhizome is used to clear heat and cool the blood, and these ingredients plays a role as the minister by reducing the heat. Red peony root promotes blood circulation and removes blood stasis to prevent blood and heat from binding, tree peony bark clears fire in blood to cool the blood and remove blood stasis, Danshen root promotes blood circulation and removes blood stasis to promote new growth, rehmannia root cools the blood and nourishes yin, and Paris rhizome cools blood and relieves itching, and these ingredients are used as assistant medicinal. Liquorice root is used as the guide to reconcile all kinds of traditional Chinese medicine. The combination of all the traditional Chinese medicine can clear heat and toxin, promote blood circulation and remove blood stasis, cool the blood and eliminate macules, and reach the skin lesions together, so that the heat toxin on the skin, texture of the skin, muscle and other body surfaces can be eliminated, and the macules and itching can be eliminated.

Psoriasis is mostly blood-heat type, which is prone to consume blood and move blood, toxic and heat flourish, and "heat" is the main factor. However, in this prescription, rehmannia root clears heat and nourishes yin, moistens dryness and produces saliva, which is mostly used clinically for yin deficiency and internal heat. Although lalang grass rhizome is classified as a blood-cooling hemostatic medicinal, it is mostly used clinically to clear lung and stomach heat, stop vomiting, stop coughing, clear bladder heat and induce diuresis. Chinese cork-tree can purge the fire of lower energizer, mostly used in the conditions of downpour of dampness-heat, and bone-steaming tiredness and fever. Paris rhizome has a little toxicity, and should not be taken in large doses for a long time. Although Paris rhizome has a good effect in clearing heat and toxin, it has no blood cooling effect, and the cost is excessively high. Danshen root not only has the function of cooling blood, but also has the ability of promoting blood circulation and removing blood stasis, and possibly a risk of bleeding (which does not facilitate erythema alleviation).

SUMMARY

The following is a summary of the subject matters described in detail herein. This summary is not intended to limit the protection scope of the present application.

The present application improves the traditional Chinese medicine composition for treating psoriasis, thus providing a novel composition of traditional Chinese medicine for treating psoriasis.

Because psoriasis is blood-heat type, toxic and heat flourish, and "heat" is the main factor. The present application is improved on the basis of the Chinese medicine compound prescription disclosed in CN1954847A, and the reason for the improvement is: rehmannia root clears heat and nourishes yin, moistens dryness and produces saliva, which is mostly used clinically for yin deficiency and internal heat. Although lalang grass rhizome is classified as a blood-cooling hemostatic medicinal, it is mostly used clinically to clear lung and stomach heat, stop vomiting, stop coughing, clear bladder heat and induce diuresis. Therefore, rehmannia root and lalang grass rhizome are removed. Chinese cork-tree can purge the fire of lower energizer, mostly used in the conditions of downpour of dampness-heat, and bone-steaming tiredness and fever. Therefore, Chinese cork-tree is removed. Paris rhizome has a little toxicity, and should not be taken in large doses for a long time. Although Paris rhizome has a good effect in clearing heat and toxin, it has no blood cooling effect, and the cost is excessively high. Danshen root not only has the function of cooling blood, but also has the ability of promoting blood circulation and removing blood stasis, and possibly a risk of bleeding (which does not facilitate erythema alleviation). In this prescription, red peony root and tree peony bark are specialized in cooling blood and promoting blood circulation, so that blood can be cooled without leaving blood stasis, so Danshen root is removed from the prescription. Garden burnet root (*Sanguisorbae radix*) with a good effect of relieving heat is added for cooling blood and hemostasis. Blood heat tends to cause bleeding, and garden burnet root has astringent effect and can stop bleeding. Through the modification of the prescription, the medicine composition is more reasonable and safe. In view of the pathogenesis of psoriasis, that is the rash develops as a result of blood heat, it specializes in clearing heat, dispelling wind, cooling blood and promoting blood circulation.

The present application is achieved by the following technical solution: a traditional Chinese medicine composition for treating psoriasis is prepared from the following traditional Chinese medicine raw materials in parts by weight:

5 to 25 parts by weight of buffalo horn powder, 5 to 15 parts by weight of Japanese honeysuckle flower (*Lonicerae japonicae Flos*; jin yin hua), 5 to 15 parts by weight of gypsum (*Gypsum fibrosum*), 2 to 10 parts by weight of red peony root (*Paeoniae radix Rubra*; chi shao), 2 to 10 parts by weight of tree peony bark (*Moutan cortex*; mu dan pi), 1 to 4 parts by weight of charred cape jasmine fruit (*Gardenias fructus Praeparatus*; jiao zhi zi), 2 to 10 parts by weight of baical skullcap root (*Scutellariae radix*; huang qin), 5 to 15 parts by weight of garden burnet root (*Sanguisorbae radix*; sheng di yu) and 0.5 to 3 parts by weight of liquorice root (*Glycyrrhizae radix* et *rhizoma*; gan cao).

Preferably, the traditional Chinese medicine composition of the present application is prepared from the following traditional Chinese medicine raw materials in parts by weight:

9 to 15 parts by weight of buffalo horn powder, 9 to 12 parts by weight of Japanese honeysuckle flower, 9 to 12 parts by weight of gypsum, 3 to 6 parts by weight of red peony root, 4 to 8 parts by weight of tree peony bark, 1 to 3 parts by weight of charred cape jasmine fruit, 2 to 6 parts by weight of baical skullcap root, 9 to 12 parts by weight of garden burnet root and 1 to 2 parts by weight of liquorice root.

More preferably, the traditional Chinese medicine composition of the present application is prepared from the following traditional Chinese medicine raw materials in parts by weight: 12 parts by weight of buffalo horn powder, 10 parts by weight of Japanese honeysuckle flower, 10 parts by weight of gypsum, 5 parts by weight of red peony root, 6 parts by weight of tree peony bark, 2 parts by weight of charred cape jasmine fruit, 5 parts by weight of baical skullcap root, 10 parts by weight of garden burnet root and 1.5 parts by weight of liquorice root.

The pharmaceutical composition of the present application can be prepared according to the following method:

Baical skullcap root, Japanese honeysuckle flower, red peony root, tree peony bark, gypsum, charred cape jasmine fruit, garden burnet root and liquorice root are weighed in proportion and decocted with water 1 to 3 times, 0.5 to 3 hours for each, 4 to 10 times quantities of water (the ratio of the volume of water to the weight of traditional Chinese medicine raw materials, in L/kg or mL/g) for each; combining the decoctions, filtering, concentrating the filtrate under reduced pressure, drying and crushing, adding the buffalo horn powder and mixing uniformly to obtain the medicine composition of the present application.

The traditional Chinese medicine composition of the present application can further contain pharmaceutically acceptable carriers as required, and can be prepared into any form of pharmaceutical preparations.

The traditional Chinese medicine composition of the present application can be in any available pharmaceutical form, such as tablets: sugar-coated tablets, thin-film-coated tablets and enteric-coated tablets; capsules: hard capsules and soft capsules; oral liquid; oral lozenge; granules; infusion granule; pills; powder; grease; pellets; suspension; pulvis; solution; injection; suppository; ointment; plaster; cream; spray; drops and patch.

The traditional Chinese medicine composition of the present application is preferably in the form of a unit dose of pharmaceutical preparation.

When the traditional Chinese medicine composition of the present application is made into a medicament, the medicament per unit dose can contain 0.1 mg to 1000 mg of the pharmaceutical active substance of the present application, and the rest is pharmaceutically acceptable carrier. The pharmaceutically acceptable carrier can be 0.01% to 99.99% of the total weight of the preparation.

When using the Chinese medicine composition, the usage and dosage are determined according to the patient's condition, such as once to three times a day. 1 to 20 tablets at a time, etc.

Preferably, the Chinese medicine composition of the present application is an oral preparation or an injection preparation.

The oral preparation is selected from one of capsules, tablets, dripping pills, granules, concentrated pills, oral liquid and mixture.

The injection preparation is selected from one of injection liquid, freeze-dried powder injection preparation and water injection preparation.

The preparation for oral administration of the Chinese medicine composition of the present application may contain common excipients, such as adhesives, fillers, diluents, tableting binders, lubricants, disintegrants, coloring agents, flavoring agents and wetting agents, and the tablets may be coated if necessary.

Suitable fillers include cellulose, mannitol, lactose and other similar fillers. Suitable disintegrants include starch, croscarmellose sodium, polyvinylpyrrolidone and starch derivatives such as sodium starch glycolate. Suitable lubricants include, for example, magnesium stearate. Suitable pharmaceutically acceptable wetting agents include sodium dodecyl sulfate.

The traditional Chinese medicine composition of the present application can be prepared into solid oral compositions by common methods such as mixing, filling and tableting. Repeated mixing can distribute the active substance throughout those compositions that use a large amount of fillers.

Oral liquid preparation can be in the form of aqueous or oil suspension, solution, emulsion, syrup or elixir, or it can be a dry product (such as oral infusion granule, oral granules, etc.), which can be reconstitute into a liquid with water or other suitable carriers before use. This liquid preparation may contain conventional additives such as suspending agents such as sorbitol, syrup, methyl cellulose, gelatin, hydroxyethyl cellulose, carboxymethyl cellulose, aluminum stearate gel or hydrogenated edible fat, emulsifiers such as lecithin, sorbitan-oleate or Arabic gum; non-aqueous carrier (which may include edible oil), such as almond oil, fractionated coconut oil, oily ester such as glycerol ester, propylene glycol, or ethanol; and preservatives, such as methyl p-hydroxybenzoate, propyl p-hydroxybenzoate or sorbic acid, and may contain conventional flavoring agents or coloring agents if necessary.

As for an injection preparation, the prepared liquid unit dosage form can contain the traditional Chinese medicine composition of the present application (as active substance) and sterile carrier. Depending on the carrier and concentration, this compound can be suspended or dissolved. The solution is usually prepared by dissolving the active substance in one or several carriers, filtering, sterilizing, and then filling it into a vial or ampoule, and sealing for storage. Excipients are for example local anesthetics, preservatives and buffers. This composition can be freeze-dried after being filled into a vial in order to improve its stability.

The traditional Chinese medicine composition of the present application can be selectively added with appropriate pharmaceutically acceptable carriers when being prepared into medicaments, wherein the pharmaceutically acceptable carriers can be selected from mannitol, sorbitol, sodium metabisulfite, sodium bisulfite, sodium thiosulfate, cysteine hydrochloride, mercaptoacetic acid, methionine, vitamin C, disodium EDTA, calcium sodium EDTA, carbonate, acetate and phosphate of monovalent alkali metals or their aqueous solutions, hydrochloric acid, acetic acid, sulfuric acid, phosphoric acid, amino acids, sodium chloride, potassium chloride, sodium lactate, xylitol, maltose, glucose, fructose, dextran, glycine, starch, sucrose, lactose, silicon derivatives, cellulose and derivatives thereof, alginate, gelatin, polyvinylpyrrolidone, glycerin, Tween 80, agar, calcium carbonate, calcium bicarbonate, polyethylene glycol, dextrin (such as cyclodextrin), steviol, phospholipid materials, kaolin, talc powder, calcium stearate, and magnesium stearate, etc.

Furthermore, the present application also discloses use of the traditional Chinese medicine composition in preparing medicaments for treating psoriasis.

The traditional Chinese medicine composition prescription of the present application has the following characteristics:

1. In the traditional Chinese medicine composition of the present application, each ingredient functions as follows:

Buffalo horn powder: it can clear the heat and toxicity in the nutrient aspect and penetrate the heat and toxicity in the blood aspect, cool the blood and eliminate erythema.

Japanese honeysuckle flower (also known as *Lonicerae japonicae Flos*) has a good effect of clearing heat and toxin, and is fragrant, penetrating and detoxificating. It can penetrate heat to the outside, so that it can discharge heat of the nutrient aspect to the outside, and promote it to penetrate qi aspect and resolve it, so as to relieve heat and toxin.

Baical skullcap root: "All kinds of heat lead to yellowing of the gallbladder, diarrhea in intestine, worsens gangrene and erode fire ulcer." "Benjin" recites that it clears heat and purges fire, dries dampness and detoxifies, swelling sore and ulcer, purges the fire of lung and stomach, so as to purge fire and detoxify.

The above three medicinals play the role as the sovereign, so as to cool the blood and dissipate blood stasis.

Red peony root: it can promote blood circulation, cool the blood and remove blood stasis, treat diseases caused by heat, and have better effect on diffusing macules than white peony. It can also clear heat in nutrients and cool the blood.

Tree peony bark (also known as *Moutan cortex*): it has the effect of cooling the blood and removing macules, clear blood and subdue fire, and prevent blood and heat from binding.

The two medicinals mentioned above play the role as the minister, which not only clear heat and cool blood, but also promote blood circulation, which can increase the efficacy of this prescription in removing macules.

Charred cape jasmine fruit: it can purge fire to relieve vexation, clear heat and facilitates diuresis, cool the blood and detoxifies, the bitter and cold nature can be made moderate after charring, the hemostatic effect can be increased, and it has an effect of cooling the blood and hemostasis.

Gypsum is pungent and sweet with cold nature, pungent nature is capable of relieving muscle, sweet nature is capable of relieving heat, it clears lung and stomach fire, penetrates muscle heat to remove macules, clears heat and purges fire, relieves vexation and thirst. “The Holy Medicine for Clearing Yang Ming’s Excess Heat”.

Garden burnet root: it is capable of promoting blood circulation and removing blood stasis, and has a good effect of cooling blood and removing macules. These three medicinals are combined to prevent blood and heat from binding, and to remove blood stasis and hemostasis and functions as the assistant.

Liquorice root: it can not only reconcile all the medicinals, but also has an effect similar to adrenocorticoid. This medicinal plays the role as the guide.

The combination of all the medicinals can clear heat and toxin, promote blood circulation and remove blood stasis, cool the blood and eliminate macules, and they reach the skin lesions together, so that the heat toxin on the skin, texture of the skin, muscle and other body surfaces can be eliminated, and the macules and itchiness can be eliminated.

The prescription of the present application is refined and the therapeutic principle is clear, which embodies the principle of “differentiating syndrome and apply treatment” in Chinese medicine, and pays attention to cooling the blood and eliminating macules, so as to achieve the effects of desquamation, stopping itching and removing macule.

2. In the prescription disclosed by the prior art CN1954847A, rehmannia root clears heat and nourishes yin, moistens dryness and produces saliva, which is mostly used clinically for yin deficiency and internal heat. Although lalang grass rhizome is classified as a blood-cooling hemostatic medicinal, it is mostly used clinically to clear lung and stomach heat, stop vomiting, stop coughing, clear bladder heat and induce diuresis. Therefore, rehmannia root and lalang grass rhizome are removed. Chinese cork-tree tends to purge the fire of lower energizer, mostly used in the conditions of downpour of dampness-heat, and bone-steaming tiredness and fever. Therefore, Chinese cork-tree is removed. Paris rhizome has a little toxicity, and should not be taken in large doses for a long time. Although Paris rhizome has a good effect in clearing heat and toxin, it has no blood cooling effect, and the cost is excessively high. Psoriasis is mostly blood-heat type, which is prone to consume blood and move blood. Danshen root not only has the function of cooling blood, but also has the ability of promoting blood circulation and removing blood stasis, and possibly a risk of bleeding (which does not facilitate erythema alleviation). In this prescription, there are already red peony root and tree peony bark, which are specialized in cooling blood and promoting blood circulation, so that blood can be cooled without leaving blood stasis, so Danshen root is removed from the prescription. Garden burnet root, which has a good effect of relieving heat, is added for cooling blood and hemostasis. Blood heat tends to cause bleeding, and garden burnet root has astringent effect and can stop bleeding. Through the modification of the prescription, the medicine composition is more reasonable and safe. In view of the pathogenesis of psoriasis, that is the rash develops as a result of blood heat, it specializes in clearing heat, dispelling wind, cooling blood and promoting blood circulation.

3. The traditional Chinese medicine composition of the present application can be used to treat the condition of psoriasis vulgaris, and the related conditions include wind-heat and dry-blood condition, wind-heat condition and internal retention of blood-heat condition.

4. The traditional Chinese medicine composition of the present application has a good therapeutic effect on psoriasis vulgaris, with the total effective rate of 96% and the total cure rate of 48%.

Other features and advantages of the present application will be set forth in the detailed description that follows, and in part will become clearer from the detailed description, or may be learned by practicing the present application. Other advantages of the present application can be realized and obtained by the solution described in the detailed description.

DETAILED DESCRIPTION

In order to make the objects, technical solutions and advantages of the present application clearer, the examples of present application will be described in detail below. It should be noted that the following examples of the present application and the features of the examples may be arbitrarily combined with each other provided that there is no confliction.

Example 1

1 kg of baical skullcap root, 2 kg of Japanese honeysuckle flower, 1 kg of red peony root, 1.2 kg of tree peony bark, 2 kg of gypsum, 0.4 kg of charred cape jasmine fruit, 2 kg of garden burnet root and 0.3 kg of liquorice root were decocted with water twice. In the first decoction, they were decocted with 8 times amount of water (79.2 L) for 1 hour. In the second decoction, they were decocted with 6 times amount of water (59.4 L) for 1.5 hours. The decoctions were combined, filtered, and the filtrate was concentrated under reduced pressure and dried. 2.4 kg of buffalo horn powder, appropriate amount of dextrin and stevioside were added to make granules, and the granules were sealed and packaged.

Example 2

0.4 kg of baical skullcap root, 1 kg of Japanese honeysuckle flower, 0.4 kg of red peony root, 0.4 kg of tree peony bark, 1 kg of gypsum, 0.2 kg of charred cape jasmine fruit, 1 kg of garden burnet root and 0.1 kg of liquorice root were decocted with water three times. In the first decoction, they were decocted with 7 times amount of water (31.5 L) for 1 hour. In the second decoction, they were decocted with 6 times amount of water (27 L) for 1 hour. In the third decoction, they were decocted with 6 times amount of water (27 L) for 1.5 hour. The decoctions were combined, filtered, and the filtrate was concentrated under reduced pressure and dried. 1 kg of buffalo horn powder, appropriate amount of dextrin and stevioside were added to make concentrated pills, and the concentrated pills were sealed and packaged.

Example 3

2 kg of baical skullcap root, 3 kg of Japanese honeysuckle flower, 2 kg of red peony root, 2 kg of tree peony bark, 3 kg of gypsum, 0.8 kg of charred cape jasmine fruit, 3 kg of garden burnet root and 0.6 kg of liquorice root were decocted with water three times. In the first decoction, they were decocted with 9 times amount of water (147.6 L) for 2 hours. In the second decoction, they were decocted with 8 times amount of water (131.2 L) for 1 hour. In the third decoction, they were decocted with 8 times amount of water (131.2 L) for 1 hour. The decoctions were combined, filtered, and the filtrate was concentrated under reduced pressure and dried. 5 kg of buffalo horn powder, appropriate amount of dextrin and stevioside were added to make tablets, and the tablets were sealed and packaged.

Example 4

1.5 kg of baical skullcap root, 2.5 kg of Japanese honeysuckle flower, 1.5 kg of red peony root, 1.5 kg of tree peony bark, 2.5 kg of gypsum, 0.6 kg of charred cape jasmine fruit, 2.5 kg of garden burnet root and 0.5 kg of liquorice root were decocted with water twice. In the first decoction, they were decocted with 10 times amount of water (131 L) for 2 hour. In the second decoction, they were decocted with 9 times amount of water (117.9 L) for 1.5 hours. The decoctions were combined, filtered, and the filtrate was concentrated under reduced pressure and dried. 3 kg of buffalo horn powder was added, mixed evenly, and 110-130 g of refined honey was added to each 100 g of powder to make big honeyed pills, and the big honeyed pills were sealed and packaged.

Example 5

0.6 kg of baical skullcap root, 1.5 kg of Japanese honeysuckle flower, 0.6 kg of red peony root, 0.6 kg of tree peony bark, 1.5 kg of gypsum, 0.3 kg of charred cape jasmine fruit, 1.5 kg of garden burnet root and 0.2 kg of liquorice root were decocted with water three times. In the first decoction, they were decocted with 5 times amount of water (34 L) for 0.5 hours. In the second decoction, they were decocted with 4 times amount of water (27.2 L) for 1 hour. In the third decoction, they were decocted with 4 times amount of water (27.2 L) for 1 hour. The decoctions were combined, filtered, and the filtrate was concentrated under reduced pressure and dried. 5 kg of buffalo horn powder and appropriate amount of dextrin were added to make capsules, and the capsules were sealed and packaged.

Example 6

0.2 kg of baical skullcap root, 0.9 kg of Japanese honeysuckle flower, 0.3 kg of red peony root, 0.4 kg of tree peony bark, 0.9 kg of gypsum, 0.1 kg of charred cape jasmine fruit, 0.9 kg of garden burnet root and 0.1 kg of liquorice root were decocted with water three times. In the first decoction, they were decocted with 5 times amount of water (34 L) for 0.5 hour. In the second decoction, they were decocted with 4 times amount of water (27.2 L) for 1 hour. In the third decoction, they were decocted with 4 times amount of water (27.2 L) for 1 hour. The decoctions were combined, filtered, and the filtrate was concentrated under reduced pressure and dried. 0.9 kg of buffalo horn powder, appropriate amount of dextrin were added to make capsules, and the capsules were sealed and packaged.

Example 7

0.6 kg of baical skullcap root, 1.2 kg of Japanese honeysuckle flower, 0.6 kg of red peony root, 0.8 kg of tree peony bark, 1.2 kg of gypsum, 0.3 kg of charred cape jasmine fruit, 1.2 kg of garden burnet root and 0.2 kg of liquorice root were decocted with water three times. In the first decoction, they were decocted with 5 times amount of water (34 L) for 0.5 hours. In the second decoction, they were decocted with 4 times amount of water (27.2 L) for 1 hour. In the third decoction, they were decocted with 4 times amount of water (27.2 L) for 1 hour. The decoctions were combined, filtered, and the filtrate was concentrated under reduced pressure and dried. 1.5 kg of buffalo horn powder and appropriate amount of dextrin were added to make capsules, and the capsules were sealed and packaged.

Beneficial Effects

In order to better illustrate the beneficial effects of the traditional Chinese medicine composition of the present application, it is demonstrated by the following testing examples.

I. Screening experiments of drug efficacy of various groups were carried out on guinea pig ear-psoriasis model.

Researching subjects: 120 clean-grade Hartley guinea pigs from 3 to 4 weeks old were provided by Beijing Huafukang Biotechnology Co., Ltd. (SCXK (Beijing) 2014-0004). The Hartley guinea pigs have weight of about 300 g, standard feed, animal room temperature 25° C. to 28° C., humidity 40% to 50%.

1. Experimental Method 1.1 Establishment of guinea pig ear-psoriasis-like animal model: 5% imiquimod cream (20 mg/cm$^2$ was applied) was evenly applied on the back of right ear of the guinea pig, three times a day for 10 days to induce psoriasis-like guinea pig ear model.

1.2 Animal grouping and medicament administration: on the basis of CN1954847A thirteen-ingredient formula (called the 13-ingredient macules-eliminating prescription), five medicinals (rehmannia root, Paris rhizome, lalang grass rhizome, Chinese cork-tree, and Danshen root) were removed in turn, and the medicinal garden burnet root was added. The various groups of modified prescriptions were as follows:

Modified prescription group 1: buffalo horn powder+Japanese honeysuckle flower+gypsum+red peony root+tree peony bark+charred cape jasmine fruit+baical skullcap root+Danshen root+liquorice root+Chinese cork-tree+lalang grass rhizome+Paris rhizome (removing rehmannia root from the 13-ingredient-prescription), and 19.52 g crude medicine/kg/d was administrated by gavage.

Modified prescription group 2: buffalo horn powder+Japanese honeysuckle flower+gypsum+red peony root+tree peony bark+charred cape jasmine fruit+baical skullcap root+Danshen root+liquorice root+Chinese cork-tree+lalang grass rhizome (removing rehmannia root and Paris rhizome from the 13-ingredient-prescription), and 19.52 g crude medicine/kg/d was administrated by gavage.

Modified prescription group 3: buffalo horn powder+Japanese honeysuckle flower+gypsum+red peony root+tree peony bark+charred cape jasmine fruit+baical skullcap root+Danshen root+liquorice root+Chinese cork-tree (removing rehmannia root, Paris rhizome and lalang grass rhizome from the 13-ingredient-prescription), and 19.52 g crude medicine/kg/d was administrated by gavage.

Modified prescription group 4: buffalo horn powder+Japanese honeysuckle flower+gypsum+red peony root+tree peony bark+charred cape jasmine fruit+baical skullcap root+Danshen root+liquorice root (removing rehmannia root, Paris rhizome, lalang grass rhizome and Chinese cork-tree from the 13-ingredient-prescription), and 19.52 g crude medicine/kg/d was administrated by gavage.

Modified prescription group 5: buffalo horn powder+Japanese honeysuckle flower+gypsum+red peony root+tree peony bark+charred cape jasmine fruit+baical skullcap root+liquorice root (removing rehmannia root, Paris rhizome, lalang grass rhizome, Chinese cork-tree and Danshen root from the 13-ingredient-prescription), and 19.52 g crude medicine/kg/d was administrated by gavage.

Modified prescription group 6: buffalo horn powder+Japanese honeysuckle flower+gypsum+red peony root+tree peony bark+charred cape jasmine fruit+baical skullcap root+liquorice root+raw garden burnet root (removing rehmannia root, Paris rhizome, lalang grass rhizome, Chinese cork-tree and Danshen root from the 13-ingredient-prescription, and adding garden burnet root thereinto), and 19.52 g crude medicine/kg/d was administrated by gavage.

In the above nine medicinals, buffalo horn powder, Japanese honeysuckle flower and baical skullcap root play a role as the sovereign; red peony root and tree peony bark play a role as the minister; charred cape jasmine fruit, gypsum and garden burnet root are used as assistants; and liquorice root plays a role as the guide.

Considering that there are still medicinals that can be removed, according to the importance of sovereign, minister, assistant, and guide, the guide, assistant and minister medicinals are removed in turn, and the following groups of modified prescriptions are obtained:

Modified prescription group 7: buffalo horn powder+Japanese honeysuckle flower+gypsum+red peony root+tree peony bark+charred cape jasmine fruit+baical skullcap root+raw garden burnet root (removing liquorice root from modified prescription group 6), and 19.52 g crude medicine/kg/d was administrated by gavage.

Modified prescription group 8: buffalo horn powder+Japanese honeysuckle flower+red peony root+tree peony bark+baical skullcap root (removing charred cape jasmine fruit, gypsum, garden burnet root and liquorice root from modified prescription group 6), and 19.52 g crude medicine/kg/d was administrated by gavage.

Modified prescription group 9: buffalo horn powder+Japanese honeysuckle flower+baical skullcap root (removing charred cape jasmine fruit, gypsum, raw garden burnet root, liquorice root, red peony root and tree peony bark from modified prescription group 6), and 19.52 g crude medicine/kg/d was administrated by gavage.

The traditional Chinese medicine raw materials shared in the above nine groups of modified prescriptions and in the 13-ingredient macules-eliminating prescription in CN1954847A had the same proportions, and the extraction method was the same as that in CN1954847A.

The above nine prescriptions were used as the experimental groups to carry out experiments at the same time, and the experiments also included: model control group: administration with equal volume of saline by gavage, and normal control group: freely drinking water and free diet. The group of the 13-ingredient macules-eliminating prescription (i.e. prepared according to the specific method in CN1954847A): 19.52 g crude medicine/kg/d was administrated by gavage.

120 guinea pigs successfully modeled were divided into 12 groups by a method using a random number table according to the above grouping, with 10 guinea pigs in each group, which were administered with the medicine continuously for 4 weeks.

1.3 Sampling: guinea pigs in the experimental groups were sacrificed after reaching the experimental observation requirements. Ear samples were taken, immersed and fixed in formalin solution for 2 days. The samples were embedded in paraffin, sliced and stained with HE.

1.4 Measurement of the thickness of the epidermis on the back of guinea pigs' ears and scoring of tissues by Baker's method.

1.4.1 Measurement of the thickness of the epidermis on the back of guinea pigs' ears: the epidermal thickness of the back of guinea pigs' ears after the establishment of psoriasis model and the intervention by metformin were measured, and the epidermal thickness of five different fields of vision (10×10) in each slice was selected, and five values were measured in each field of vision, then their respective average value was calculated and statistically analyzed.

1.4.2 Baker's method for scoring tissue: HE stained sections were taken for collecting images under microscope, 5 visual fields in each group were randomly selected, and then histopathological changes were scored by Baker's method. Each slice was scored according to the pathological scoring standard of psoriasis vulgaris, and the comprehensive score of pathological changes was statistically analyzed. The evaluation criteria of histological score of psoriasis by Baker's method are shown in Table 1 below:

TABLE 1

Baker's scoring standard

| | Items | Histological scoring (points) |
|---|---|---|
| Stratum corneum | Munro microabscess | 1.5 |
| | Parakeratosis | 0.5 to 1.5 (mild to severe) |
| | Hyperkeratosis | 0.5 |
| Epidermal layer | Epidermal processes extend into a rod shape | 0.5 to 1.5 (mild to severe) |
| | Spinous layer hypertrophy | 1.0 |
| | Particle layer disappearance | 1.0 |
| Dermal cortex | Inflammatory cell infiltration | 0.5 to 1.5 (mild to severe) |
| | Upward clubbing of mastoid process | 1.0 |
| | Capillary dilatation | 0.5 |

2. Statistical processing: the experimental data is expressed as ($\bar{x}$±S), which is processed by SPSS17 software. The mean of the two samples were compared by t test, $P<0.05$ means significant difference, and $P<0.01$ means highly significant difference.

3. Experimental Results:

3.1 General Conditions:

In the normal control group, guinea pigs have docile behavior and are mentally normal with thick hair and skin luster in both ears, and they have normal drinking, diet and defecation. The guinea pigs in the model control group scratched their ears after 2 weeks, and the hair on the back of the ears where the medicine was applied is partially shed, and the skin on the back of the ears of some animals is reddened, and the capillaries are obviously dilated. After 4 weeks, the hair shedding, vasodilation and ear scratching of guinea pigs in the model control group are aggravated. The above symptoms are significantly alleviated after 4 weeks of gavage administration in the group of 13-ingredient macules-eliminating prescription and the experimental group (groups of modified prescriptions 1 to 9), and modified prescription group 6 in the experimental group shows the most significant improvement. The improvement effect of 13-ingredient macules-eliminating prescription group, modified prescription groups 1-5 and modified prescription groups 7-9 is weaker than that of modified prescription group 6.

Morphology of both ears: guinea pigs in the normal control group have thick hairs and normal skin. Ear skin symptoms of the model guinea pigs in the control group after 4 weeks: hair shedding, rough skin, local capillary dilation, reddish skin, etc. appeared where 5% imiquimod cream was applied. It was observed that hair shedding was reduced, capillary dilatation was reduced, and local pigmentation appeared after 4 weeks of gavage administration in the 13-ingredient macules-eliminating prescription group and modified prescription groups 1-9. Modified prescription group 6 has the most significant improvement in symptoms. The improvement effect of 13-ingredient-macules-eliminating-prescription group, modified prescription groups 1-5 and modified prescription groups 7-9 is less effective than that of modified prescription group 6.

2. Measurement of the Thickness of the Epidermis on the Back of Guinea Pigs' Ears and the Results of Scoring the Tissues by Baker's Method:

Measurements of the thickness of the epidermis on the back of guinea pigs' ears are shown in Table 2. Compared with the normal control group, the thickness of the epidermis on the back of guinea pigs' ears in the model control group is significantly increased (P<0.001), which indicates that the modeling is successful. Compared with the model control group, the thickness of the epidermis on the back of guinea pigs' ears in the 13-ingredient macules-eliminating prescription group and modified prescription groups 1-9 decreased significantly (P<0.05), with the most significant symptom improvement for modified prescription group 6 (P<0.001), and modified prescription group 6 has significant difference with respect to 13-ingredient macules-eliminating prescription group (P<0.05). Compared with modified prescription groups 1-5 and modified prescription groups 7-9, modified prescription group 6 has significant improvement (P<0.05).

The results of Baker scoring are shown in Table 3. Compared with the normal control group, the Baker score in the model control group is significantly increased (P<0.001), which indicates that the modeling is successful. Compared with the model group, the Baker score in the 13-ingredient macules-eliminating prescription group and modified prescription groups 1-9 decreased significantly (P<0.05), wherein the most significant symptom improvement was in modified prescription group 6 (P<0.001), and modified prescription group 6 has significant difference with respect to 13-ingredient macules-eliminating prescription group (P<0.05). Compared with modified prescription groups 1-5 and modified prescription groups 7-9, modified prescription group 6 has significant improvement (P<0.05) and significant difference. It is suggested from the results that modified prescription group 6 can significantly improve the pathological changes of guinea pig ear psoriasis model, and the therapeutic effect is significantly better than that of the 13-ingredient macules-eliminating prescription group.

The above experimental results show that, after removing rehmannia root, Paris rhizome, lalang grass rhizome, Chinese cork-tree and Danshen root, while adding garden burnet root on the basis of the original 13-ingredient macules-eliminating prescription, the inhibitory effect on guinea pig ear psoriasis model can be significantly enhanced (P<0.05). On this basis, however, the inhibitory effect on guinea pig ear psoriasis model was significantly weakened after the guide medicinal (liquorice root), assistant medicinals (charred cape jasmine fruit, gypsum, raw garden burnet root) and minister medicinals (red peony root and tree peony bark) were removed in turn (P<0.05). Therefore, modified prescription group 6 is the relatively good modified prescription screened out.

TABLE 2

Measurement of the thickness of the epidermis on the back of guinea pigs' ears

| Groups | Number of animals | Dosage | Thickness of epidermis (μm) |
|---|---|---|---|
| Normal control group | 10 | — | 57.29 ± 5.12f |
| Model control group | 10 | — | 165.21 ± 12.13a |
| 13-ingredient macules-eliminating prescription group | 10 | 19.52 g crude medicine/kg | 74.08 ± 3.21d |
| Modified prescription group 1 | 10 | 19.52 g crude medicine/kg | 77.82 ± 2.85d |
| Modified prescription group 2 | 10 | 19.52 g crude medicine/kg | 75.39 ± 4.96d |
| Modified prescription group 3 | 10 | 19.52 g crude medicine/kg | 76.76 ± 4.51d |
| Modified prescription group 4 | 10 | 19.52 g crude medicine/kg | 78.21 ± 5.10d |
| Modified prescription group 5 | 10 | 19.52 g crude medicine/kg | 75.44 ± 2.46d |
| Modified prescription group 6 | 10 | 19.52 g crude medicine/kg | 69.32 ± 1.18e |
| Modified prescription group 7 | 10 | 19.52 g crude medicine/kg | 92.74 ± 6.42c |
| Modified prescription group 8 | 10 | 19.52 g crude medicine/kg | 118.17 ± 1.94c |
| Modified prescription group 9 | 10 | 19.52 g crude medicine/kg | 127.24 ± 8.51b |

Note:
As for the letters a-f, the same letter indicates that there is no significant difference between the two groups (p > 0.05).

TABLE 3

Baker scoring method results on histology

| Groups | Number of animals | Dosage | Baker scoring (score) |
|---|---|---|---|
| Normal control group | 10 | — | 0.57 ± 0.12f |
| Model control group | 10 | — | 6.02 ± 0.86a |
| 13-ingredient macules-eliminating prescription group | 10 | 19.52 g crude medicine/kg | 1.30 ± 0.05d |
| Modified prescription group 1 | 10 | 19.52 g crude medicine/kg | 1.53 ± 0.11d |
| Modified prescription group 2 | 10 | 19.52 g crude medicine/kg | 1.32 ± 0.04d |
| Modified prescription group 3 | 10 | 19.52 g crude medicine/kg | 1.43 ± 0.06d |
| Modified prescription group 4 | 10 | 19.52 g crude medicine/kg | 1.61 ± 0.03d |
| Modified prescription group 5 | 10 | 19.52 g crude medicine/kg | 1.59 ± 0.04d |
| Modified prescription group 6 | 10 | 19.52 g crude medicine/kg | 1.05 ± 0.01e |
| Modified prescription group 7 | 10 | 19.52 g crude medicine/kg | 2.96 ± 0.15c |

TABLE 3-continued

| Baker scoring method results on histology | | | |
|---|---|---|---|
| Groups | Number of animals | Dosage | Baker scoring (score) |
| Modified prescription group 8 | 10 | 19.52 g crude medicine/kg | 3.38 ± 0.62b |
| Modified prescription group 9 | 10 | 19.52 g crude medicine/kg | 4.53 ± 1.02b |

Note:
As for the letters a-f, the same letter indicates that there is no significant difference between the two groups ($p > 0.05$).

4. Conclusion:

In view of the above, compared with the model control group and each modified prescription group, the modified prescription group 6 (buffalo horn powder+Japanese honeysuckle flower+gypsum+red peony root+tree peony bark+charred cape jasmine fruit+baical skullcap root+raw garden burnet root+liquorice root) can significantly improve the symptoms on appearance and pathological changes of guinea pig ear psoriasis model, significantly reduce local inflammatory response and reduce local vasodilation. There was significant difference compared with the original 13-ingredient macules-eliminating prescription group. The therapeutic effect of modified prescription group 6 on guinea pig ear psoriasis model was significantly enhanced. Through this experiment, it is confirmed that the original 13-ingredient macules-eliminating prescription group has significantly enhanced efficacy of improving the guinea pig ear psoriasis model when having the five medicinals of rehmannia root, Paris rhizome, lalang grass rhizome, Chinese cork-tree and Danshen root removed, and having garden burnet root added at the same time. That is, the 9-ingredient macules-eliminating prescription (buffalo horn powder+Japanese honeysuckle flower+gypsum+red peony root+tree peony bark+charred cape jasmine fruit+baical skullcap root+raw garden burnet root+liquorice root) can replace the 13-ingredient macules-eliminating prescription to play an anti-psoriasis role.

Through the above screening experiments, it is found that the medicine composition of the present application (9-ingredient macules-eliminating prescription) has a preliminary anti-psoriasis effect, and the following experiments can be further carried out.

II. Pharmacodynamic Experiment of the Medicine Composition of the Present Application on Mice Psoriasis-Like Skin Lesion Model Induced by Imiquimod.

Researching subjects: SPF Grade, Female C57BL/6 mice, weighing 18 g to 20 g, provided by Shanghai Slac Experimental Animal Co., Ltd. (2015000562136). The mice were fed with standard diet and the animal room was kept at the temperature of 23±2° C. and the humidity of 40% to 70%.

Experimental Method

Animal grouping: 70 female C57BL/6 mice were randomly divided into 7 groups according to their body weight, with 10 mice in each group: group 1 is the blank control group, group 2 is the model group, group 3 is the methotrexate (Shanghai Xinyi Pharmaceutical Factory) group, group 4 is the prior art product in the market Yujinyinxie Tablet (Shaanxi Xiangju Pharmaceutical Co., Ltd.) group, and groups 5 to 7 are the 9-ingredient macules-eliminating prescription groups prepared by the method of Example 1 of the present application, among which group 5 is the high-dosage group of 9-ingredient macules-eliminating prescription, group 6 is the medium-dosage group of 9-ingredient macules-eliminating prescription, and group 7 is the low-dosage group of 9-ingredient macules-eliminating prescription.

The high-dose group of 9-ingredient macules-eliminating prescription: daily dosage of crude medicine for human use was 61.5 g/day (extracted by the method of Example 1, the extraction rate was about 0.52), and the high-dose group was twice the clinical equivalent dose. The medium-dosage group of 9-ingredient macules-eliminating prescription: clinical equivalent dose. The low-dosage group of 9-ingredient macules-eliminating prescription: the dosage in the low-dosage group was ¼ of that in the high-dosage group.

TABLE 4

| Grouping and administration | | | | | | | |
|---|---|---|---|---|---|---|---|
| Groups | Group: medicine | Animal Number | Extract dosage (g of extract/ kg) | Administration volume (ml/kg) | Administration concentration of the extract (g/ml) | Administration route | Administration frequency * cycle |
| 1 | Blank control group | 10 | — | 10 | — | i.g. | Qd * 1 weeks |
| 2 | Model group: sterile water | 10 | — | 10 | | i.g. | Qd * 1 weeks |
| 3 | Methotrexate group | 10 | 1 mg/kg | 10 | 0.1 mg/ml | i.g. | Qd * 1 weeks |
| 4 | Yujinyinxie tablet group | 10 | 0.72 g/kg | 10 | 0.072 | i.g. | Qd * 1 weeks |
| 5 | High-dosage group of 9-ingredient macules-eliminating prescription | 10 | 11.24 | 10 | 1.124 | i.g. | Qd * 1 weeks |
| 6 | Middle-dosage group of 9-ingredient macules-eliminating prescription | 10 | 5.62 | 10 | 0.562 | i.g. | Qd * 1 weeks |

TABLE 4-continued

| Grouping and administration | | | | | | | |
|---|---|---|---|---|---|---|---|
| Groups | Group: medicine | Animal Number | Extract dosage (g of extract/ kg) | Administration volume (ml/kg) | Administration concentration of the extract (g/ml) | Administration route | Administration frequency * cycle |
| 7 | Low-dosage group of 9-ingredient macules-eliminating prescription | 10 | 2.81 | 10 | 0.281 | i.g. | Qd * 1 weeks |

Modeling method and treatment: After C57BL/6 mice had their back hair shaved (the area was about 2.5 cm×2.5 cm), 80 μl of 5% imiquimod cream was applied to the shaved area of each mouse once a day for one week. At the same time of modeling, the corresponding medicine was subjected to intragastrical (I.G.) administration orally once a day for 7 days. 24 hours after the seventh topical application of imiquimod cream and the corresponding medicine, the skin of lesion was taken, fixed with 10% formalin, embedded in paraffin, sliced, stained with HE, and was pathologically scored (epidermal thickness, epidermal cell keratinization degree, dermal thickness and dermal inflammatory cell infiltration degree).

Experimental Observation

Clinical symptoms: observe any clinical symptoms of each animal at the beginning and during the experiment. Any abnormal response should be recorded.

Measurement Indicator

1) Overall observation score of skin lesion (PASI method): once a day, a trend line was plotted, and the change of skin lesions of mice in each group was observed.

PASI method: photos of the skin lesions were taken every day, and the erythema, scales and infiltration thickening degree at the skin lesions were scored, and the three scores were added up to obtain the total scores.

PASI scoring standard: 0, none; 1 point, mild; 2 points, moderate; 3 points, severe; and 4 points, extremely severe.

2) At the end of the experiment, samples were taken at local skin lesions, fixed with HE staining, and pathologically scored (epidermal thickness, epidermal cell keratinization degree, dermal thickness and dermal inflammatory cell infiltration degree).

End of experiment: after the experiment, the animals were sacrificed by $CO_2$ deep anesthesia, and the corresponding tissues were collected.

Statistics of data: the experimental data are expressed by Mean±SD, and the data between two groups are tested by T test, P<0.05 is considered as significant difference.

Experimental Results:

1) The effect of gavage of 9-ingredient macules-eliminating prescription for 7 days on the weight of C57BL/6 mice model with psoriasis of back skin induced by imiquimod.

Imiquimod-treated mice were given extract of the high, medium and low-dosage (11.24 g extract/kg, 5.62 g extract/kg and 2.81 g of extract/kg) of 9-ingredient macules-eliminating prescription by gavage for 7 days and it has no significant effect on the weight, and there was no statistically significant difference compared with the model group (Table 5). As for the positive medicine methotrexate group (1 mg/kg), imiquimod-treated mice were given methotrexate by gavage for 7 days and it reduced the weight, and there was a statistically significant difference compared with the model group (P<0.05 or P<0.01 v.s model group).

TABLE 5

The effect of gavage of the 9-ingredient macules-eliminating prescription for 7 days on the weight of C57BL/6 mice model with psoriasis of back skin induced by imiquimod ($\bar{x} \pm s$)

| Groups | Extract dosage (g of extract/kg) | N (Number of animals) | BW (g) Day 1 | BW (g) Day 8 |
|---|---|---|---|---|
| Blank control group | — | 10 | 20.10 ± 0.60 | 21.07 ± 1.20 |
| Model group | — | 10 | 20.04 ± 0.37 | 20.61 ± 1.01 |
| Methotrexate group | 1 mg/kg | 10 | 20.29 ± 0.68 | 17.99 ± 2.71* |
| Yujinyinxie tablet group | 0.72 g/kg | 10 | 20.06 ± 0.66 | 20.62 ± 0.97 |
| High-dosage group of 9-ingredient macules-eliminating prescription | 11.24 | 10 | 20.54 ± 0.65 | 20.25 ± 1.17 |
| Medium-dosage group of 9-ingredient macules-eliminating prescription | 5.62 | 10 | 20.25 ± 0.42 | 20.79 ± 0.27 |
| Low-dosage group of 9-ingredient macules-eliminating prescription | 2.81 | 10 | 20.36 ± 0.63 | 20.77 ± 1.03 |

*P < 0.05 v.s model group

2) The effect of gavage administration of the 9-ingredient macules-eliminating prescription for 7 days on the total observation score of skin lesion of C57BL/6 mice model with psoriasis of back skin induced by imiquimod.

On the 4th day of modeling, erythema, scales and increased skin thickness were observed on the back skin of model group mice, and there was a statistically significant difference in the total score compared with the blank control group (P<0.01 v.s blank control group). The results show that imiquimod induced the C57BL/6 mouse back skin psoriasis model successfully.

Gavage administration in high (11.24 g of extract/kg), medium (5.62 g of extract/kg) and low-dosages (2.81 of g extract/kg) of 9-ingredient macules-eliminating prescription for 7 days has improvement visible to naked eye on the skin lesions of C57BL/6 mouse back skin psoriasis model induced by 5% imiquimod. The total score of skin lesions from day 4 to day 8 is lower than that of the model group, and there was a statistically significant difference compared with the model group (P<0.01 or 0.05 v.s the model group).

TABLE 6

The effect of gavage of the 9-ingredient macules-eliminating prescription for 7 days on the total score of skin lesion of C57BL/6 mice with psoriasis of back skin induced by imiquimod ($\bar{x} \pm s$)

| Groups | Extract dosage (g of extract/kg) | N(Number of animais) | Severity index Day 4 | Day 5 | Day 6 | Day 7 | Day 8 |
|---|---|---|---|---|---|---|---|
| Blank control group | — | 10 | 0.00 ± 0.00** | 0.00 ± 0.00** | 0.00 ± 0.00** | 0.00 ± 0.00 | 0.00 ± 0.00 |
| Model group | — | 10 | 1.75 ± 0.59 | 2.70 ± 0.54 | 3.55 ± 0.64 | 5.10 ± 0.64## | 5.30 ± 2.56## |
| Methotrexate group | 1 mg/kg | 10 | 1.65 ± 0.58 | 2.20 ± 0.48* | 1.90 ± 0.39** | 3.60 ± 0.63 | 3.05 ± 1.82* |
| Yujinyinxie tablet group | 0.72 g/kg | 10 | 1.45 ± 0.44 | 1.90 ± 0.66** | 1.75 ± 0.79** | 2.50 ± 0.53** | 2.65 ± 2.06* |
| High-dosage group of 9-ingredient macules-eliminating prescription | 11.24 | 10 | 1.15 ± 0.41* | 1.40 ± 0.61** | 1.70 ± 0.42** | 3.00 ± 0.39* | 2.50 ± 1.26** |
| Middle-dosage group of 9-ingredient macules-eliminating | 5.62 | 10 | 1.11 ± 0.46* | 1.46 ± 0.86** | 1.73 ± 0.79** | 3.04 ± 0.49* | 2.46 ± 1.02** |
| Low-dosage group of 9-ingredient macules-eliminating | 2.81 | 10 | 1.65 ± 0.75 | 1.95 ± 0.55** | 2.20 ± 0.67** | 3.05 ± 0.40* | 3.70 ± 1.75* |

*P < 0.05 v.s model group,
**P < 0.01 v.s model group;
P < 0.01 v.s blank control group 3) The Effect of Gavage of 9-Ingredient Macules-Eliminating Prescription for 7 Days on Pathological Changes of Skin of C57BL/6 Mice Model with Psoriasis of Back Skin Induced by Imiquimod The results of HE staining shows that excessive keratinization of the epidermis, epidermal thickening, dermal thickening and inflammatory cell infiltration were found in the mice of the model group, and there was a statistically significant difference compared with the blank control group (P<0.01 v.s blank control group), which indicated that imiquimod successfully induced the C57BL/6 mouse back skin psoriasis model.

Compared with the model group, the pathological results of mice skin in the high-dosage group (11.24 g of extract/kg) and the medium-dosage group (5.62 g of extract/kg) of the 9-ingredient macules-eliminating prescription shows that the keratinization of epidermal cells and the degree of epidermal thickening are significantly reduced, with statistically significant differences (P<0.05 v.s the model group), while the degree of dermal thickening and dermal inflammatory cell infiltration are slightly reduced, but there is no statistically significant difference (P>0.05 v.s the model group). Compared with the model group, the total skin pathological score of mice in the high-dosage group (11.24 g extract/kg) and the medium-dosage group (5.62 g extract/kg) of the 9-ingredient macules-eliminating prescription is significantly lower, with statistically significant difference (P<0.01 v.s the model group). The results show that gavage administration for 7 days in the high-dosage group (11.24 g extract/kg) and the middle-dosage group (5.62 g extract/kg) of the 9-ingredient macules-eliminating prescription has obvious improvement on the pathology of psoriasis on the back skin of C57BL/6 mice induced by imiquimod (Table 7).

TABLE 7

The effect of gavage of the 9-ingredient macules-eliminating prescription for 7 days on the skin lesions of C57BL/6 mice model with psoriasis on back skin induced by imiquimod ($\overline{x}$ ± s)

| | | | Pathological score | | | | |
|---|---|---|---|---|---|---|---|
| Groups | Extract dosage (g of extract/kg) | N (Number of anim | Epidermal cell keratinization | Epidermal thickness | Dermal thickness | Dermal inflammatory cells infiltration degree | Total score |
| Blank control group | — | 10 | 0.00 ± 0.00 | 0.00 ± 0.00 | 0.00 ± 0.00 | 0.00 ± 0.00 | 0.00 ± 0.00 |
| Model group | — | 10 | 2.40 ± 0.70## | 2.00 ± 0.47## | 1.90 ± 0.57## | 1.50-0.53## | 7.80 ± 1.40## |
| Methotrexate group | 1 mg/kg | 10 | 1.60 ± 0.84* | 1.60 ± 0.52, p = 0.09 | 1.50 ± 0.53 | 1.10 ± 0.32, p = 0.05 | 5.80 ± 1.14** |
| Yujinyinxie tablet group | 0.72 g/kg | 10 | 1.50 ± 0.53** | 1.50 ± 0.53* | 1.60 ± 0.52 | 1.30 ± 0.48 | 5.90 ± 1.20** |
| High-dosage groupof 9-ingredient macules-eliminating prescription | 11.24 | 10 | 1.10 ± 0.88** | 1.50 ± 0.67* | 1.60 ± 0.52 | 1.10 ± 0.63 | 5.30 ± 1.96** |
| Middle-dosage group of 9-ingredient macules-eliminating prescription | 5.62 | 10 | 1.15 ± 0.71** | 1.48 ± 0.35 | 1.63 ± 0.52 | 1.17 ± 0.41 | 5.43 ± 0.82** |
| Low-dosage groupof 9-ingredient macules-eliminating prescription | 2.81 | 10 | 2.10 ± 0.74 | 1.60 ± 0.52, p = 0.09 | 1.70 ± 0.48 | 1.50 ± 0.53 | 6.90 ± 1.10 |

*P < 0.05 v.s model group,
**P < 0.01 v.s model group;
P < 0.01 v.s blank control group Conclusion: gavage administration of the 9-ingredient macules-eliminating prescription for 7 days at 11.24 g/kg and 5.62 g/kg has obvious improvement on the psoriasis of C57BL/6 mice back skin induced by imiquimod. Moreover, the efficacy of the medium-dosage group (5.62 g/kg) is equivalent to that of the high-dosage group (11.24 g/kg), indicating that when the dosage is increased to a certain extent, the efficacy will not increase significantly and there may be a risk of increasing toxicity. Gavage administration of 9-ingredient macules-eliminating prescription for 7 days at 2.81 g/kg has a weak improvement effect on the psoriasis of C57BL/6 mice back skin induced by imiquimod. The relatively good dosage of the 9-ingredient macules-eliminating prescription is 5.62 g/kg, that is, daily dosage of 61.5 g for human.

III. Study on Long-Term Toxicity of the 9-Ingredient Macules-Eliminating Prescription and 13-Ingredient Macules-Eliminating Prescription to Normal Rats Experiment animals: ninety SPF grade male SD rats, weighing from 150 g to 200 g, were used and provided by Beijing Huafukang Biotechnology Co., Ltd. (SCXK (Beijing) 2014-0004). They were fed with standard diet, and the animal room was kept at the temperature of 25° C. to 28° C. and the humidity of 40% to 50%.

Experimental Method:

Animal Grouping and Administration:

90 SD rats were randomly divided into groups with 30 rats in each group. Normal group was given 10 mL/kg/d of normal saline every day by gavage, the dosage in the 9-ingredient macules-eliminating prescription group (prepared according to the method of Example 1 of the present application) was 64.1 g crude medicine/kg, and the dosage of the 13-ingredient macules-eliminating prescription group (prepared according to the method in the embodiment of CN1954847A) was 219.8 g crude medicine/kg. The rats were administrated continuously for 12 weeks, and given standard feed and purified water, and the weight, diet and water intake of the rats were measured and recorded every day. At the 12th week, ⅔ of the animals were sacrificed and dissected. The administration of medicine was suspended for the remaining ⅓ animals in each group and continued to observe for 2 weeks, and the treatment was the same as mentioned before. They were fasted but drank water for 12 hours before sacrifice.

Sampling

Blood sampling: Blood was taken from femoral artery of each rat into 10 mL EP tubes, centrifuged at 3500 rpm/10 min, and the supernatant was stored in −20° C. refrigerator for later use.

Tissue sampling: the rats were weighed and cut off on their necks for sacrifice, and the visceral organ index was calculated.

$$\text{Visceral organ index}=(\text{visceral organ weight}/\text{body weight})\times 1000$$

Biochemical Index Test

Liver function test: alanine aminotransferase (ALT) kit, aspartate aminotransferase (AST) kit, alkaline phosphatase (ALP) kit and γ-glutamyltranspeptidase (γ-GGT) kit, purchased from Nanjing Jiancheng Bioengineering Research Institute Co., Ltd., were used for testing.

Kidney function test: Urea nitrogen (BUN) kit purchased from Nanjing Jiancheng Bioengineering Research Institute Co., Ltd. and creatinine (Cr) kit purchased from Shanghai Baili Biotechnology Co., Ltd. were used for testing.

Statistical processing: the experimental data is expressed as ($\bar{x}$±S), which is processed by SPSS17 software. The mean of the two samples were compared by t test, P<0.05 means significant difference, and P<0.01 means highly significant difference.

Experimental Results:

General Physiological Index

Compared with the normal group, after 10 weeks of administration, the weight of the 13-ingredient macules-eliminating prescription group decreased significantly (P<0.05), but there was no significant change in the 9-ingredient macules-eliminating prescription group, and the weight of the rats in the 9-ingredient macules-eliminating prescription group was higher than that in the 13-ingredient macules-eliminating prescription group.

From around the 6th week, compared with the normal group, the water intake of rats in the 13-ingredient macules-eliminating prescription group decreased significantly (P<0.05); At the eighth week, the water intake of rats in the 9-ingredient macules-eliminating prescription group tended to decrease, but there was no significant difference, and it was significantly higher than that of rats in the 13-ingredient macules-eliminating prescription group (P<0.05).

During the whole experiment, starting from around the 8th week, the food intake of the 13-ingredient macules-eliminating prescription group was significantly lower than that of the normal group (P<0.05), and there was no significant difference between the 9-ingredient macules-eliminating prescription group and the normal group (P>0.05).

After two weeks the medicine was suspended, the weight, water intake and food intake of rats in the 9-ingredient macules-eliminating prescription group showed a significant recovery trend, and recovered to the level that had no significant difference compared with the normal group (P>0.05). The weight, water intake and food intake of rats in the 13-ingredient macules-eliminating prescription group showed a recovery trend in the recovery period after two weeks the medicine was suspended, but the recovery was not obvious, and there was a significant difference compared with the normal group (P<0.05).

TABLE 8

Changes of weight, water intake and food intake of male rats in long-term toxicity test

| Time (weeks) | Weight (g) | | | Water intake (g) | | | Food intake (g) | | |
|---|---|---|---|---|---|---|---|---|---|
| | Normal group | 9-ingredient macules-eliminating prescription group | 13-ingredient macules-eliminating prescription group | Normal group | 9-ingredient macules-eliminating prescription group | 13-ingredient macules-eliminating prescription group | Normal group | 9-ingredient macules-eliminating prescription group | 13-ingredient macules-eliminating prescription group |
| 0 | 168.00 ± 5.51a | 169.67 ± 2.73a | 167.67 ± 2.03a | — | — | — | — | — | — |
| 2 | 213.67 ± 4.10a | 215.33 ± 8.25a | 202.33 ± 8.09a | 39.88 ± 2.38b | 40.18 ± 4.86b | 40.43 ± 4.14b | 24.52 ± 0.74a | 25.58 ± 0.84a | 25.43 ± 0.90a |
| 4 | 311.67 ± 15.30a | 309.67 ± 9.33a | 300.00 ± 8.33a | 48.92 ± 2.55a | 49.67 ± 2.12a | 42.79 ± 10.13a | 25.05 ± 1.05a | 30.02 ± 1.08a | 25.44 ± 0.48a |
| 6 | 343.33 ± 12.71a | 339.00 ± 15.04a | 320.33 ± 15.31a | 48.90 ± 0.40a | 48.70 ± 3.98a | 34.10 ± 5.14b | 26.17 ± 0.40a | 24.92 ± 4.34a | 22.41 ± 3.26a |
| 8 | 405.67 ± 6.06a | 388.67 ± 14.55a | 362.33 ± 4.91a | 49.71 ± 1.13 a | 46.17 ± 0.48 a | 27.00 ± 2.31c | 26.69 ± 0.37a | 26.12 ± 1.09a | 20.00 ± 1.15b |
| 10 | 447.67 ± 2.60a | 431.67 ± 16.48a | 386.67 ± 14.68b | 47.00 ± 0.14a | 44.00 ± 4.47 a | 32.38 ± 1.23b | 27.88 ± 0.13a | 21.28 ± 0.07a | 19.55 ± 2.11b |
| 12 | 461.60 ± 1.19a | 440.53 ± 10.05a | 401.41 ± 4.21b | 48.64 ± 0.72a | 40.78 ± 1.14a | 33.68 ± 2.38 b | 25.27 ± 0.59a | 26.80 ± 2.37a | 15.93 ± 1.60b |
| Recovery period after two weeks of suspending the medicine | 472.24 ± 4.35a | 465.87 ± 5.7a | 408.39 ± 6.42b | 47.37 ± 1.23a | 46.64 ± 2.5 a | 35.91 ± 3.47b | 27.77 ± 0.67a | 27.01 ± 1.43a | 17.32 ± 1.48b |

a-c: represent that there is no significant difference for the same letters.

Visceral organ index: After 90 days of gavage, the rats in each group were sampled. Visceral organ index comparison: the liver and kidney indexes of rats in the 13-ingredient macules-eliminating prescription group were significantly higher than those in the normal group (P<0.05), but there was no significant difference among other groups. Two weeks after the medicine was suspended, the liver and kidney indexes of rats in the 13-ingredient macules-eliminating prescription group showed a recovery trend, but they were still significantly higher than those in the normal group (P<0.05).

TABLE 9

Results of visceral organ index in rats

| Measurement Indicator | Time | Normal group | 9-ingredient macules-eliminating prescription group | 13-ingredient macules-eliminating prescription group |
|---|---|---|---|---|
| Cardiac index | 12 weeks | 1.23 ± 0.01 | 1.26 ± 0.02 | 1.24 ± 0.01 |
| | Recovery period after two weeks of suspending the medicine | 1.25 ± 0.02 | 1.26 ± 0.01 | 1.25 ± 0.04 |
| Lung index | 12 weeks | 1.36 ± 0.05 | 1.47 ± 0.10 | 1.58 ± 0.11 |
| | Recovery period after two weeks of suspending the medicine | 1.34 ± 0.06 | 1.40 ± 0.08 | 1.53 ± 0.13 |
| Liver index | 12 weeks | 10.10 ± 0.42 | 10.18 ± 0.13 | 12.86 ± 0.48* |
| | Recovery period after two weeks of suspending the medicine | 10.13 ± 0.21 | 10.15 ± 0.22 | 12.47 ± 0.38* |
| Thymus index | 12 weeks | 0.30 ± 0.02 | 0.27 ± 0.02 | 0.32 ± 0.03 |
| | Recovery period after two weeks of suspending the medicine | 0.31 ± 0.01 | 0.28 ± 0.02 | 0.28 ± 0.01 |
| Spleen index | 12 weeks | 0.52 ± 0.03 | 0.55 ± 0.06 | 0.51 ± 0.03 |
| | Recovery period after two weeks of suspending the medicine | 0.53 ± 0.41 | 0.55 ± 0.07 | 0.50 ± 0.02 |
| Stomach index | 12 weeks | 1.90 ± 0.03 | 1.98 ± 0.05 | 1.97 ± 0.08 |
| | Recovery period after two weeks of suspending the medicine | 1.91 ± 0.01 | 1.94 ± 0.02 | 1.96 ± 0.05 |
| Kidney index | 12 weeks | 2.48 ± 0.09 | 2.26 ± 0.05 | 2.70 ± 0.09* |
| | Recovery period after two weeks of suspending the medicine | 2.45 ± 0.07 | 2.27 ± 0.01 | 2.65 ± 0.01* |

*Compared with the normal group, there was significant difference (P < 0.05)

Enzymology test of serum for liver and kidney function of rats: After 12 weeks of administration, compared with the normal group, the contents of ALP, ALT, AST/γ-GGT in the serum of rats in the 13-ingredient macules-eliminating prescription group were significantly increased (P<0.05, P<0.001). 2 weeks after the administration of medicine was suspended, the contents of ALP, ALT, and AST/γ-GGT all had a decreasing trend, but there were still significant differences compared with the normal group (P<0.05, P<0.001). As for the 9-ingredient macules-eliminating prescription group, only the AST content in serum increased significantly, while the others did not change significantly, and recovered to normal level after 2 weeks of suspension of the administration. It shows that long-term administration of the 13-ingredient macules-eliminating prescription has harmful effects on the liver function of rats, while the 9-ingredient macules-eliminating prescription has low toxicity and is easy to recover to normal after suspension of the administration. At the same time, compared with the normal group, the contents of BUN and Cr in the serum of rats in the 13-ingredient macules-eliminating prescription group were significantly increased, but there was no significant change in the 9-ingredient macules-eliminating prescription group. This indicates that long-term administration of the 13-ingredient macules-eliminating prescription has harmful effects on the liver function of rats, while the 9-ingredient macules-eliminating prescription has no such toxic and side effects.

TABLE 10

Results of enzymology test of serum for liver and kidney function in rats

| Measurement Indicator | Time | Normal group | 9-ingredient macules-eliminatin gprescription group | 13-ingredient macules-eliminat ing prescription group |
|---|---|---|---|---|
| ALP(U/gprot) | 12 weeks | 8.51 ± 0.28 | 8.51 ± 0.78 | 11.04 ± 0.69* |
| | Recovery period after two weeks of suspending the medicine | 8.53 ± 0.14 | 8.50 ± 0.32 | 10.38 ± 0.54* |
| ALT(U/gprot) | 12 weeks | 12.24 ± 4.75 | 18.56 ± 1.54 | 41.29 ± 8.23* |
| | Recovery period after two weeks of suspending the medicine | 12.27 ± 2.14 | 14.39 ± 3.65 | 35.11 ± 6.91 |
| AST(U/gprot) | 12 weeks | 141.7 ± 15.5 | 161.3 ± 0.2* | 244.7 ± 3.4** |
| | Recovery period after two weeks of suspending the medicine | 142.5 ± 11.2 | 150.2 ± 5.4 | 209.3 ± 4.1* |
| γ-GGT(U/L) | 12 weeks | 12.32 ± 4.14 | 16.44 ± 3.27 | 35.66 ± 7.27* |
| | Recovery period after two weeks of suspending the medicine | 12.01 ± 2.20 | 14.39 ± 2.87 | 29.37 ± 5.14* |
| BUN(mmol/L) | 12 weeks | 447.8 ± 8.1 | 467.4 ± 7.6 | 591.2 ± 75.1** |
| | Recovery period after two weeks of suspending the medicine | 449.5 ± 5.4 | 455.9 ± 8.2 | 553.0 ± 23.4** |
| Cr(μmol/L) | 12 weeks | 53.79 ± 0.57 | 56.16 ± 6.00 | 64.57 ± 2.91* |
| | Recovery period after two weeks of suspending the medicine | 50.34 ± 2.38 | 54.03 ± 4.99 | 61.21 ± 0.38* |

*represents that there is significant difference compared with the normal group ($P < 0.05$);
**represents that there is a highly significant difference compared with the normal group ($P < 0.001$)

Conclusion: Through long-term observation of general physiological indexes and visceral organ indexes and testing of serum enzymes related to liver and kidney function of rats in each group, it is found that the 13-ingredient macules-eliminating prescription group could induce the increase of liver and kidney indexes inrats, which has a significant impact on serum enzymes related to liver and kidney function. It indicates that long-term administration of the 13-ingredient macules-eliminating prescription could cause liver and kidney toxicity. However, the 9-ingredient macules-eliminating prescription group has low toxicity, no obvious effect after long-term administration, and it is easy to recover to normal level after suspending the medicine. This result may be related to the fact that the 13-ingredient macules-eliminating prescription contains Paris rhizome, which is slightly toxic and belongs to the liver meridian, and has toxic and side effects after long-term and large dose administration.

IV. Clinical Experimental Data of the 9-Ingredient Macules-Eliminating Prescription 1. Case Selection (1) Diagnostic Criteria ① Diagnostic Criteria of Psoriasis Vulgaris:

"Guiding Principles of Clinical Research on New Traditional Chinese Medicine", "Criteria for Diagnosis and Efficacy of Common Diseases" (China Traditional Chinese Medicine Press, October 1999), "Criteria for Diagnosis and Improvement of Clinical Diseases" (People's Military Medical Press, June 1998) were referred to. The skin lesions caused by this disease are mainly red inflammatory papules, maculopapules and patches of different sizes, covered with multilayer of silvery-white scales. A bright film can be seen after the scales are scraped off, and there may be punctate bleeding under the film (Auspitz sign).

The rash can be in the form of drops, coins, maps and mixtures, etc., with obvious boundary.

Rash can appear all over the body surface. When the rash appears in the scalp, the hair is bunched; and when the rash appears on the nail plate (fingers, toes), there may be punctate pits in the shape of thimble or the nail plate is uneven, yellow and thickens.

It may be accompanied by different degrees of itching.

② Diagnostic Criteria of Blood-Heat Psoriasis in Syndrome of Chinese Medicine:

Related types include wind-heat and dry-blood condition, wind-heat condition and internal retention of blood-heat condition; lesioned and red skin; continuously increasing or rapidly expanding of new rashes; upset and irritable; mouth parched and tongue scorched; yellow urine; red or crimson tongue; slip or rapid pulse.

(2) Inclusion Criteria

① age from 16 to 65, male or female;

② meet the diagnostic criteria of psoriasis vulgaris;

③ diagnosed as blood-heat type psoriasis by traditional Chinese medicine syndrome differentiation; and ④ the patient agrees and signs the informed consent form.

(3) Exclusion Criteria

① pregnant or lactating women;

② allergic to the present medicine, or allergic to a medicinal ingredient;

③ internally administrated with a steroid drug within recent 2 weeks;

④ internally administrated with a retinoic acid drug or externally applied with a steroid preparation within 1 week;

⑤ being treated with monoclonal antibody or other biological immunotherapy;

⑥ combined with serious primary diseases of cardiovascular, cerebrovascular, liver, renal and hematopoietic system, etc., and patients with mental illness.

⑦ other cases that do not comply with the inclusion criteria.

2. Experimental Method (1) Research methods: random open method was used.

(2) Medicine used for the treatment: 9-ingredient macules-eliminating prescription; medicine prescription: baical skullcap root, Japanese honeysuckle flower, buffalo horn powder, red peony root, tree peony bark, raw garden burnet root, gypsum, charred cape jasmine fruit, and liquorice root (prepared according to the method of Example 1 of the present application).

(3) Treatment Method:

Two sachets (14 g for each sachet) were taken orally each time, twice a day, and the treatment period was 2 months to 3 months.

(4) Observation Indicators

Safety Indicators:

① examination of general physical examination items,

② blood and urine routine examinations were performed before and after the treatment, ③ ECG, liver and kidney functions were examined before and after the treatment, ④ possible adverse responses, including clinical symptoms, measurement index, severity, elimination methods of adverse responses, and objective evaluation of other safety issues.

Therapeutic Effect Index:

Psoriasis lesion area and severity index (PAST) was used to score the improvement of symptoms of patients before and after the treatment: the area size and severity of scales, infiltration and erythema lesions in different parts (head and neck, torso, and upper and lower limbs) of patients were recorded before and after the treatment.

(5) Criteria of Therapeutic Effect

The therapeutic effect of patients before and after the treatment was evaluated by PASI score. Therapeutic effect index=(total PASI score before treatment-total PASI score after treatment)/total PASI score before treatment*100%.

Clinical cured: the therapeutic effect index is greater than 95%

Notable effect: the therapeutic effect index is 75% to 95%

Improvement: the therapeutic effect index is 50% to 75%

Effective rate=(number of clinically cured cases in statistics+number of notably effective cases in statistics+number of improvement cases in statistics)/number of cases in statistics×100%.

Proportion of patients of PASI-75 (PASI score decreased by at least 75%). PASI-75 is the leading method to evaluate the efficacy of clinical trials of medicine treatment for psoriasis internationally.

3. Results (1) General information: A total of 100 cases were observed, including 52 males and 48 females, with an average age of 44 years (ranging from 18 years to 62 years) and an average course of disease of 11.3 years (ranging from 1 year to 40 years). Among them, 17 cases were mild, 35 cases were moderate and 48 cases were severe.

(2) Therapeutic Effect Results

Results are shown as Table 11, the total cure rate is 48%, the total effective rate is 96%, and the proportion of PASI-75 patients is 78%. The cure rate is 23.5% and the effective rate is 100% for mild patients; the cure rate is 62.9% and the effective rate is 100% for moderate patients, and the cure rate is 45.8% and the effective rate is 91.7% for severe patients. The medicine of the present application has a high effective rate for psoriasis of different degrees, mild, moderate and severe, and the cure rate of moderate and severe patients is greater than that of mild patients.

TABLE 11

Therapeutic effect results

| | Clinically cured Number of cases % | Notable effect Number of cases % | Improvement Number of cases % | Proportion of PASI-75 patients Number of cases % | Effective rate Number of cases % |
|---|---|---|---|---|---|
| Mild | 4 | 5 | 8 | 9 | 17 |
| | 23.5 | 29.4 | 47.1 | 52.9 | 100 |
| Moderate | 22 | 8 | 5 | 30 | 35 |
| | 62.9 | 22.9 | 14.2 | 85.7 | 100 |
| Severe | 22 | 17 | 5 | 39 | 44 |
| | 45.8 | 35.4 | 10.4 | 81.3 | 91.7 |
| Total | 48 | 30 | 18 | 78 | 96 |
| | 48.0 | 30.0 | 18.0 | 78.0 | 96.0 |

(3) Safety Results

① there is no abnormal safety index of patients during and after treatment;

② 100 cases have no obvious adverse responses.

③ the 9-ingredient macules-eliminating prescription is generally well tolerated, and there is no serious adverse response of liver and renal functions and blood system.

④ transaminase of 3 patients was slightly higher than normal value, which has no clinical significance.

⑤ the red blood cells and hemoglobin of male patients tend to decrease, which has no clinical significance.

4. Conclusion

The traditional Chinese medicine composition of the present application can be used for condition of psoriasis vulgaris, and the related types include wind-heat and dry-blood condition, wind-heat condition and internal retention of blood-heat condition. The medicine has a good therapeutic effect on psoriasis vulgaris, with a total effective rate of 96% and a total cure rate of 48%. The proportion of patients of PASI-75 (PASI score decreased by 75%) is 78%, and the therapeutic effect is comparable to the current monoclonal antibody drugs that antagonize TNF-α and interleukin IL for treating psoriasis.

The efficacy index of psoriasis treatment medicine counted in the references is PASI-75 (PASI score decreased by 75%). At present, the monoclonal antibody drugs for treating psoriasis, such as Adalimumab (Xiumeile), Infiximab (Leike), Ustekinumab, Sucekinumab (Sujin) and so on, achieve a proportion of PASI-75 patients of 70%-80%, comparable to the therapeutic effect of the traditional Chinese medicine composition of the present invention on psoriasis vulgaris (with a proportion of PASI-75 patients of 78%).

To sum up, the traditional Chinese medicine granules of the present application for treating psoriasis vulgaris are convenient to use, have no obvious side effects, have good therapeutic effect and low cost, and it is a relatively good choice for treating psoriasis vulgaris of blood-heat type. On the basis of the prior art, the traditional Chinese medicine composition of the present application has improved prescription, it does not contain precious medicinal materials or toxic medicinal materials, reduces the cost and toxic and side effects, and does not reduce the curative effect. Compared with monoclonal antibody drugs, the traditional Chinese medicine composition of the present application has low treatment cost, good safety and better pharmacoeconomic value than monoclonal antibody drugs.

The invention claimed is:

1. A medicine composition for treating psoriasis, consisting of the following medicine raw materials in parts by weight:

5 to 25 parts by weight of buffalo horn powder, 5 to 15 parts by weight of Japanese honeysuckle flower, 5 to 15 parts by weight of gypsum, 2 to 10 parts by weight of red peony root, 2 to 10 parts by weight of tree peony bark, 1 to 4 parts by weight of charred cape jasmine fruit, 2 to 10 parts by weight of baical skullcap root, 5 to 15 parts by weight of garden burnet root and 0.5 to 3 parts by weight of liquorice root, wherein the medicine composition is prepared by the following steps: weighing baical skullcap root, Japanese honeysuckle flower, red peony root, tree peony bark, gypsum, charred cape jasmine fruit, garden burnet root and liquorice root, decocting with water 1 to 3 times, 0.5 to 3 hours for each, 4 to 10 times quantities of water for each; combining the decoctions, filtering, concentrating the filtrate under reduced pressure, drying, adding the buffalo horn powder and mixing uniformly.

2. The medicine composition according to claim 1, wherein the medicine composition consists of the following medicine raw materials in parts by weight:

9 to 15 parts by weight of buffalo horn powder, 9 to 12 parts by weight of Japanese honeysuckle flower, 9 to 12 parts by weight of gypsum, 3 to 6 parts by weight of red peony root, 4 to 8 parts by weight of tree peony bark, 1 to 3 parts by weight of charred cape jasmine fruit, 2 to 6 parts by weight of baical skullcap root, 9 to 12 parts by weight of garden burnet root and 1 to 2 parts by weight of liquorice root.

3. The medicine composition according to claim 1, wherein the medicine composition consists of the following medicine raw materials in parts by weight:

12 parts by weight of buffalo horn powder, 10 parts by weight of Japanese honeysuckle flower, 10 parts by weight of gypsum, 5 parts by weight of red peony root, 6 parts by weight of tree peony bark, 2 parts by weight of charred cape jasmine fruit, 5 parts by weight of baical skullcap root, 10 parts by weight of garden burnet root and 1.5 parts by weight of liquorice root.

4. A pharmaceutical preparation comprising the medicine composition according to claim 1, wherein the pharmaceutical preparation is in any pharmaceutical preparation form.

5. The pharmaceutical preparation according to claim 4, wherein the pharmaceutical preparation is in a form as follows:

tablet, capsule, oral lozenge, granule, pill, powder, grease, pellets, suspension, solution, injection, suppository, ointment, spray, drops, drop pill, or patch.

6. The pharmaceutical preparation according to claim 4, wherein the pharmaceutical preparation form is an oral preparation.

7. The pharmaceutical preparation according to claim 4, wherein the pharmaceutical preparation comprises a pharmaceutically acceptable carrier, and the weight of the pharmaceutically acceptable carrier is 0.01% to 99.99% of the total weight of the pharmaceutical preparation.

8. A method of treating psoriasis, comprising administering the medicine composition according to claim 1.

9. The method according to claim 8, wherein the psoriasis is psoriasis vulgaris.

* * * * *